US005976876A

United States Patent [19]
Canfield et al.

[11] Patent Number: 5,976,876
[45] Date of Patent: Nov. 2, 1999

[54] ANTIBODIES SPECIFIC FOR HLH β CORE FRAGMENT

[75] Inventors: Robert E. Canfield, Cold Spring, N.Y.; Steven Birken, Dumont, N.J.; John O'Connor, New Rochelle; Galina Kovalevskaya, New York, both of N.Y.

[73] Assignee: The Trustees of Columbia University in the City of New York, New York, N.Y.

[21] Appl. No.: 08/763,669

[22] Filed: Dec. 11, 1996

Related U.S. Application Data

[60] Provisional application No. 60/008,502, Dec. 11, 1995.

[51] Int. Cl.$^6$ .............................. C07K 16/26; C12N 5/12
[52] U.S. Cl. ......................... 435/336; 435/326; 435/346; 530/387.1; 530/388.24; 530/389.2
[58] Field of Search ........................... 530/388.24, 389.2, 530/387.1; 435/346, 326

[56] References Cited

U.S. PATENT DOCUMENTS

| | | |
|---|---|---|
| 4,565,687 | 1/1986 | Khazaeli et al. . |
| 4,804,626 | 2/1989 | Bellet et al. . |
| 4,851,356 | 7/1989 | Canfield et al. . |
| 5,356,817 | 10/1994 | Cole . |
| 5,445,968 | 8/1995 | Blithe et al. . |
| 5,674,983 | 10/1997 | Blithe et al. . |

OTHER PUBLICATIONS

Birken, S. et al. Endocrin. 133: 983–989, Sep. 1993.
Iles, R. K. et al. J. Endocrin. 133:459–466, Sep. 1992.
Harlow, E. et al. Antibodies, A Laboratory Manual, CSHL, Cold Spring Harbor, N. Y., pp. 72–77, 92–97, 128–135, and 141–157, 1988.
Weir, D.M. et al. vol. 1 Immunochemistry, Blackwell Scientific Publications, Boston, MA., pp. 8.14–8.15, 1986.
Armstrong, et al. 1984. Use of a highly sensitive and specific immunoradiometric assay for detection of human chorionic gonadotropin in urine of normal, nonpregnant and pregnant individuals. *J. Clin. Endocrinol. Met.* 59:867–874 (Exhibit A).
Barbé, F. et al. 1995. undetectable luteinizing hormone levels using a monoclonal immunometric assay. *J. Endocrinol. Invest.* 18(1):806–808 (Exhibit B).
Birken, S., et al. 1993. Structure and significance of human luteinizing hormone–beta core fragment purified from human pituitary extracts. *Endocrinology*. 133(3):985–989 (Exhibit C).
Blithe, et al. 1988. Purification of β–core fragment from pregnancy urine and demonstration that its carbohydrate moieties differ from those of native human chorionic gonadotropin–β *Endocrinology* 122: 173–180 (Exhibit D).
Cole, L.H., et al. 1988. Urinary human chorionic gonadotropin free β–subunit and β–core fragment: a new marker of gynecological cancers. *Cancer Research* 48: 1356–1360 (Exhibit E).

Costagliola, S. et al. 1994. Glycoprotein hormone isomorphism and assay discrepancy: the paradigm of luteinizing hormone (LH). [Review]. *J. Endocrinol. Invest.* 17(4):291–9(Exhibit F).
Iles, R.K. et al. 1992. Immunoreactive beta–core–like material in normal postmenopausal urine: human chorionic gonadotropin or LH origin? Evidence for the existence of LH core *J. Endocrinol.* 133 (3): 459–466 (Exhibit G).
Kardana, et al. 1988. Urinary gonadotropin peptide–isolation and purification and its immunohistochemical distribution in normal and neoplastic tissues. *British Journal of Cancer* 58: 281–286 (Exhibit H).
Krichevsky, A. et al. 1988. Preparation and Characterization of antibodies to the urinary fragment of the human chorionic gonadotropin beta–subunit. *Endocrinology* 123(1): 584–593 (Exhibit I).
Martin–Du–Pan, R.C. et al. 1994. Clinical significance of invisible or partially visible luteinizing hormone. *Hum. Reprod.* 9(11):1987–1990 (Exhibit J).
Moyle, W.R. et al. 1982. Use of monoclonal antibodies to subunits of human chorionic gonadotropin to examine the orientation of the hormone in its complex with receptor. *PNAS* 79: 2245–2249 (Exhibit K).
Neven, P. et al. 1993. Substantial urinary concentrations of material resembling beta–core fragment of chorionic gonadotropin beta–subunit in mid–menstrual cycle. *Clin. Chem.* 39 (9):1857–1860 (Exhibit L).
O'Connor, et al. 1988. Development of highly sensitive immunoassays to measure human chorionic gonadotropin, its β subunit and β core fragment in the urine: application to malignancies. *Cancer Research* 48:1361–1366 (Exhibit M).
Pettersson, K. et al. 1991. Monoclonal antibody–based discrepancies between two–site immunometric tests for lutropin. *Clin. Chem.* 37(10:Pt. 1): 1745–1748 (Exhibit N).
Prentice, L.G. and Ryan, R.J. 1975. LH and its subunits in human pituitary, serum and urine. *J. Clin. Endocrinol. Metab.* 40:2 303–312 (Exhibit O).
Romani, P. et al. 1977. Biologically active luteinizing hormone (LH) in plasma: II. Comparison with immunologically active LH levels throughout the human menstrual cycle. *Acta Endocrinol (Copenh)* 84:4 697–712 (Exhibit P).

*Primary Examiner*—Christina Y. Chan
*Assistant Examiner*—Phillip Gambel
*Attorney, Agent, or Firm*—John P. White; Cooper & Dunham LLP

[57] ABSTRACT

This invention provides an antibody which specifically binds to hLHβcf without cross-reacting with hLH, hLHβ or hCGβcf. In an embodiment, the monoclonal antibody is designated B505. In a further embodiment, the hybridoma cell line producing the monoclonal antibody B 505 is designated ATCC Accession No.12000. This invention provides different uses of the antibodies. Finally, this invention provides a method for determining the amount of hLHβcf or hLHβcf-related molecule in a sample.

2 Claims, 10 Drawing Sheets

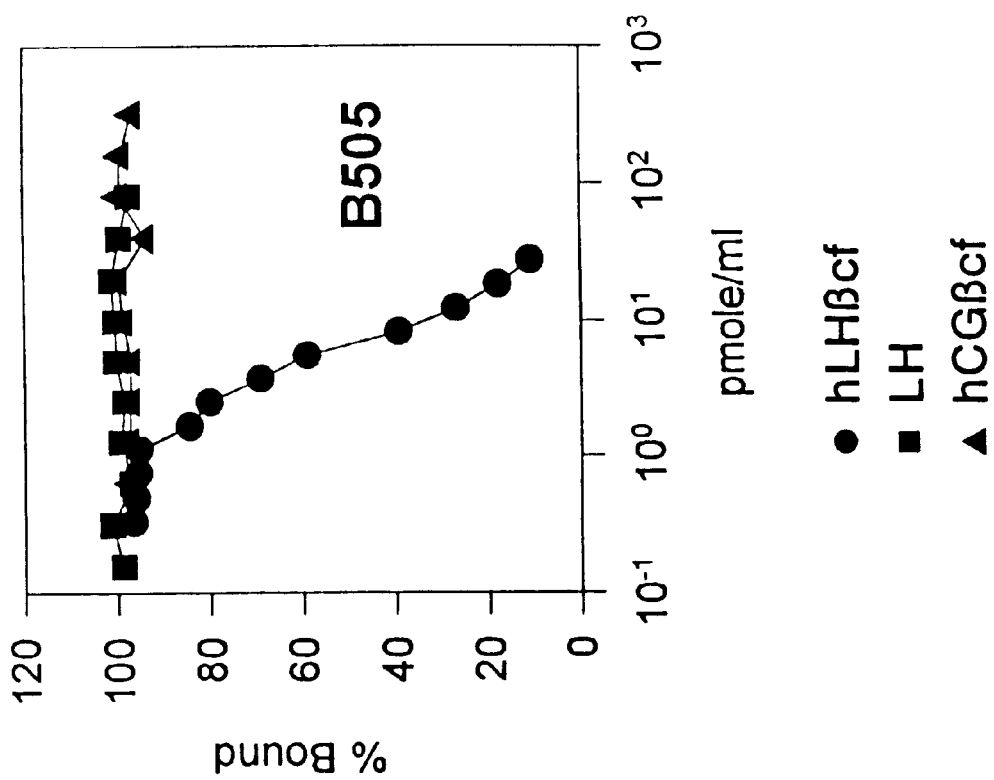
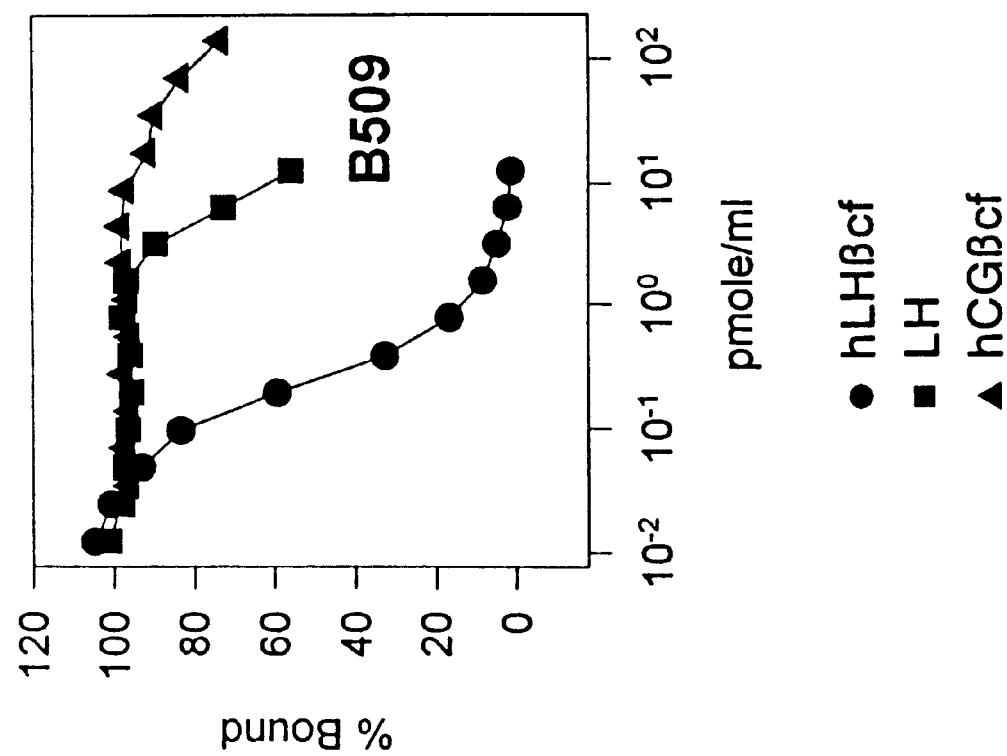

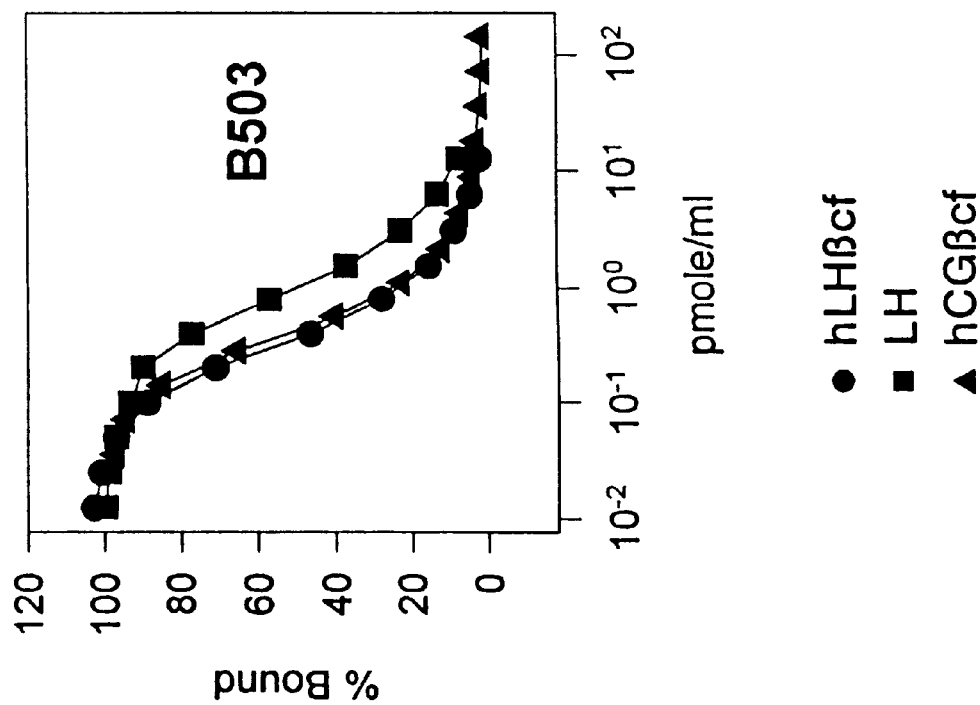
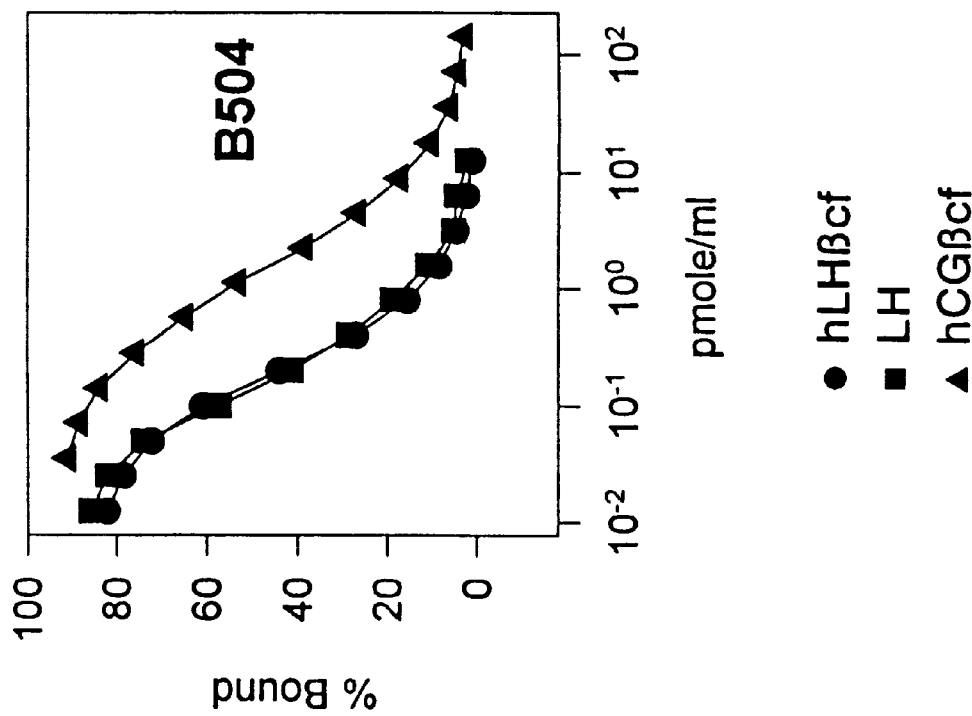

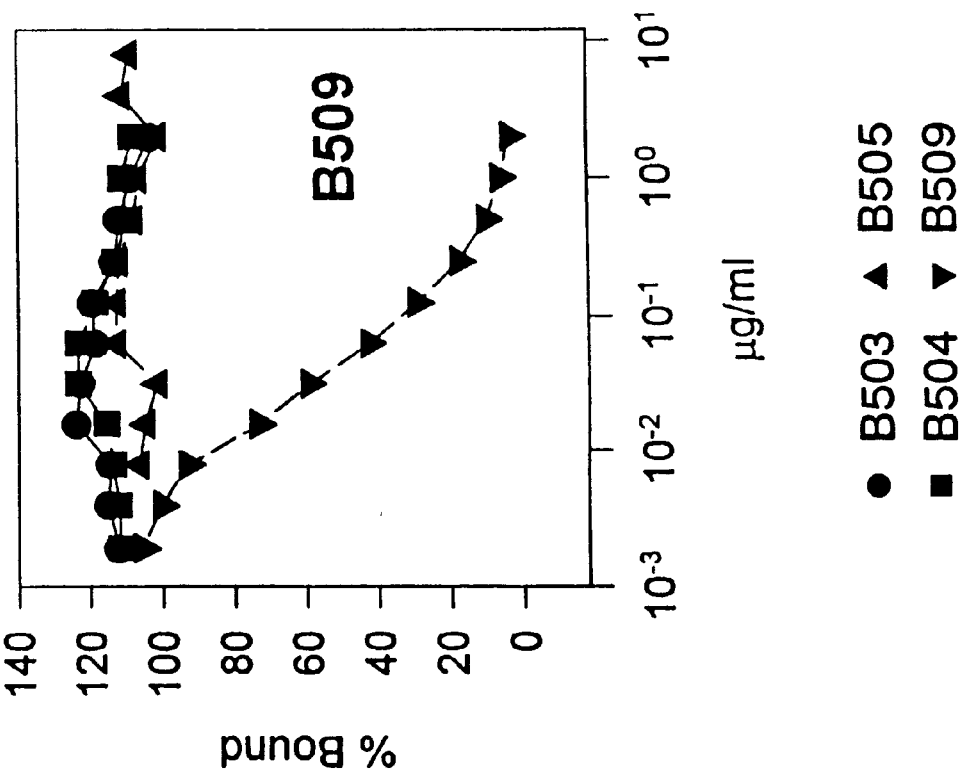
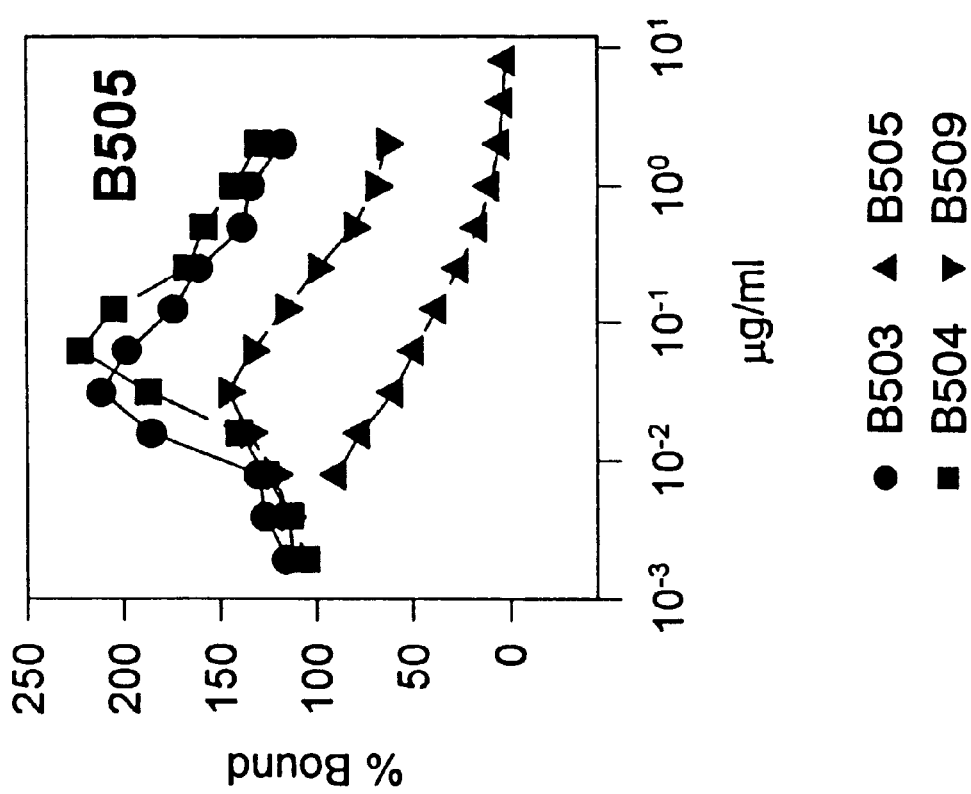

HPLC elution positions of the pituitary and urinary hLHbf

○ Pituitary B505 activity (hLHbf)
● Periovulatory urine B505 activity

Immunoreactivity testing of pituitary hLHbf after HPLC column in assay for hLHbf (B505-B503) and in assay for hCG bf (B210-B108)

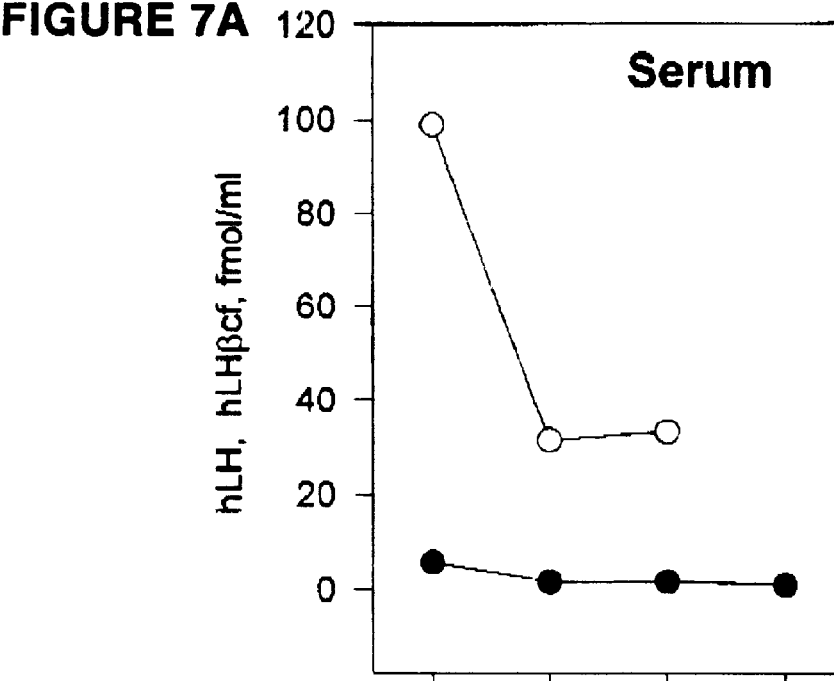
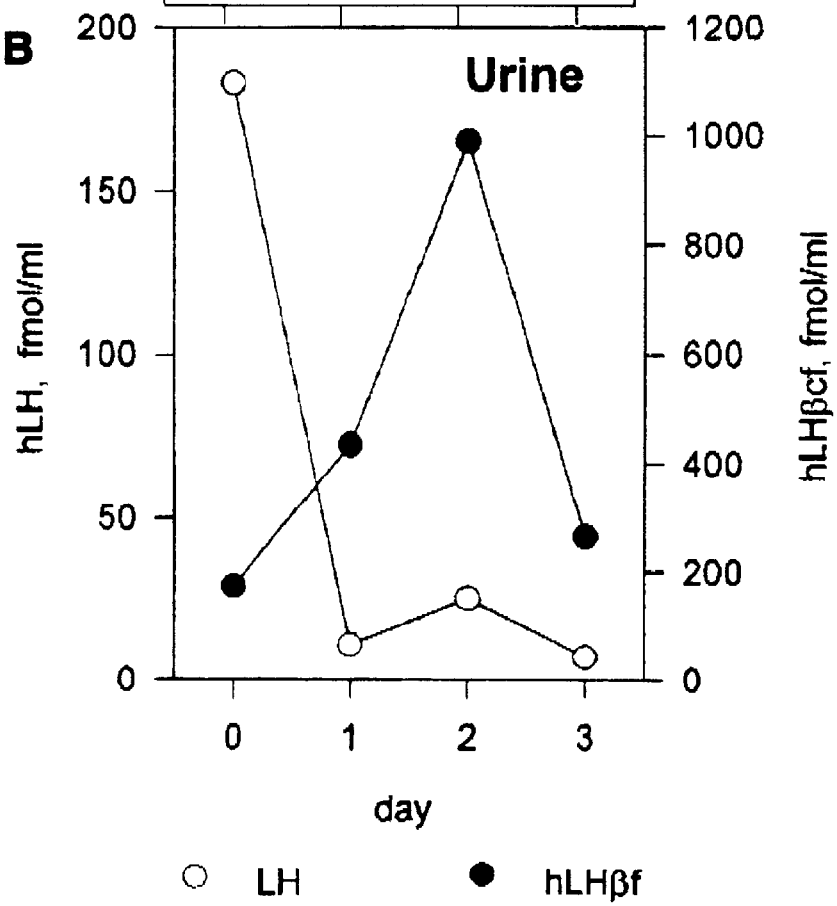
FIGURE 7A
FIGURE 7B
day 0 is the day of LH surge

ANTIBODIES SPECIFIC FOR HLH β CORE FRAGMENT

This application claims priority of U.S. provisional application No. 60/008,502, filed Dec. 11, 1995, the content of which is hereby incorporated into this application by reference.

The invention disclosed herein was made with United States Government support under National Institute of Health Grants, HD 15454 and ES-07589. Accordingly, the United States Government has certain rights in this invention.

Throughout this application, various references are referred to within parentheses. Disclosures of these publications in their entireties are hereby incorporated by reference into this application to more fully describe the state of the art to which this invention pertains. Full bibliographic citations for these references may be found at the end of this application, preceding the claims.

BACKGROUND OF THE INVENTION

Recently, applicants isolated an hLH beta core fragment (hLHβcf) from human pituitaries. This molecule is homologous to the hCG beta core fragment (hCGβcf), which may be a marker of normal pregnancy, Down syndrome, and certain cancers. Applicants now report antibodies to the hLHβcf, four of which have been applied in sensitive immunoradiometric assays for urinary measurements. One of the antibodies recognizes an epitope on the hLHβcf, which is not present on the hCGβcf, hLH, or hLH,. This specific hLHβcf antibody acts cooperatively with other newly-developed antibodies reported here to produce an assay with a sensitivity of 1 fmol/ml of hLHβcf. The specificity of these new IRMA systems will make it possible to measure the hLHβcf in urine in the presence of hLH, hLH beta, or the hCGβcf. Although the hLHβcf used to develop specific antibodies was purified from pituitaries, the assays developed recognize this metabolite in urine. Measurements of heterodimeric hLH as compared to hLHβcf in the urine of cycling women indicated that the concentration of hLHβcf rose as high as 6–7 times the concentration of hLH starting a day after the midcycle surge. The new measuring systems allow the precise quantitation of this hLH metabolite in urine.

Understanding of the metabolites of the gonadotropins excreted into urine may help to distinguish between healthy and abnormal physiological states. For example, the hCG β core fragment (hCGβcf) is present at high levels in the urine of normal pregnant women (Kato et al., 1988) but, also, occurs abnormally in the urine of nonpregnant patients with a variety of malignancies (O'Connor et al., 1988, Cole et al., 1988a,1988b,1990). Applicants and others have observed a beta core fragment of hLH (hLHβcf) in the urine of normally cycling women shortly after the hLH midcycle surge (Neven et al., 1993) and in the urine of postmenopausal women (Iles et al., 1992). Both the hCG and hLH fragments have analogous structures (Birken et al., 1993) but, it has not been possible to measure one of the fragments in the presence of the other. For example, the utility of the hCGβcf molecule as a marker of malignancies in postmenopausal women has been compromised by the cross-reactions of antibodies elicited to the hCGβcf with a molecule of similar structure and size (presumably the homologous fragment of hLH) excreted by normal postmenopausal women in their urine. Consequently, the high threshold measurement compromised the ability of hCGβcf to serve as a cancer marker in this important patient population. Applicants had earlier suggested the hypothesis that, if it were possible to distinguish an hLHβcf from an hCGβcf, a preponderance of the former might be indicative of the normal state while a major mole fraction of the hCG fragment may be associated with malignancy (Birken et al., 1993). Immunological analysis of the hLHβcf in normal cycling women, as compared with infertile patients, may identify a metabolic marker associated with an abnormal state (mean ovulatory cycles, polycystic ovarian disease). For these reasons, applicants have developed a series of antibodies to the hLHβcf, which was isolated from a pituitary extract but, as reported here, can also be used to measure such a molecule in urine.

Although antibodies to the hCGβcf could be used to extract the hLH-associated core materials from normal postmenopausal women, it was difficult to generate sufficient material to even characterize the structure of the molecule present in urine. Instead, applicants were able to successfully isolate an hLHβcf from human pituitary extracts (Birken et al., 1993). Using this material, applicants now report the development and characterization of immunometric measurement systems to quantitate the pituitary hLHb core fragment in urine. These assays will now make it possible to evaluate the metabolism of hLH in both pre and postmenopausal women and to possibly distinguish between normal and abnormal physiological states.

SUMMARY OF THE INVENTION

This invention provides an antibody which specifically binds to hLHβcf without cross-reacting with hLH, hLHβ or hCGβcf. In an embodiment, the monoclonal antibody is designated B505. In a further embodiment, the hybridoma cell line producing the monoclonal antibody B 505 is designated ATCC Accession No.HB-12000. This invention also provides hLHβcf antibody which competitively inhibits the binding of the monoclonal antibody B505.

This invention provides a method for determining the amount of hLHβcf in a sample comprising steps of: (a) contacting at least one capturing antibody selected from a group consisting of B503, B504 and B509 with a solid matrix under conditions permitting binding of capturing antibody with the solid matrix; (b) contacting the bound matrix with the sample under conditions permitting binding of the antigen present in the sample with the capturing antibody; (c) separating the bound matrix and the sample; (d) contacting the separated bound matrix with an antibody which specifically binds to hLHβcf without cross reacting with hLH, hLHβ or hCGβcf; and (e) determining the amount of bound antibody on the bound matrix, thereby determining the amount of hLHβcf in the sample. In an embodiment, the antibody is B505.

In performing the above method, the separation of the bound matrix and the sample in step (c) may be carried out by: (i) removing of the sample from the matrix, and (ii) washing the bound matrix with an appropriate buffer. Alternatively, they may be separated by other methods known in the art.

This invention also provides a method of detecting ovulation in a female subject comprising: (a) obtaining samples from the female subject; and (b) determining the amount of hLHβcf in the samples, the presence of a peak of hLHβcf indicating the occurrence of ovulation.

This invention further provides the above method, wherein step (b) comprising: (i) contacting the sample with an antibody which specifically binds to hLHβcf without cross-reacting with hLH, hLHβ or hCGβcf under conditions permitting formation of complex between the antibody and hLHβcf; and (ii) determining the amount of the complex, thereby determining the amount of hLHβcf in the samples. This invention further provides the above method, wherein the antibody is labelled with a detectable marker.

This invention provides a method for reducing the amount of hLHβcf in a sample comprising steps of: (a) contacting the sample with an antibody which specifically binds to hLHβcf without cross-reacting with hLH, hLHβ or hCGβcf under conditions permitting formation of complex between the antibody and hLHβcf; and (b) removing the complex formed, thereby reducing the amount of hLHβcf in the sample.

This invention also provides the above method, wherein the removing step comprising: (i) contacting the complex with protein A under conditions permitting formation of a complex of protein A with an antibody; and (ii) removing the complex formed, thereby reducing the amount of hLHβcf in the sample.

In an embodiment of this method, the complex is contacted with a secondary antibody under conditions permitting binding of the secondary antibody to the first antibody prior to step (i). In a separate embodiment of this method, the antibody is linked to a solid matrix.

This invention further provides samples with reduced amount of hLHβcf produced by the above-described methods.

BRIEF DESCRIPTION OF THE FIGURES

FIG. 2 Liquid phase competition curves of the binding of $^{125}$I-hLHβcf with unlabeled hLHβcf, hLH, hCGβcf is shown for the four antibodies: B509, B504, B503, B505. Panel B shows the most specific antibody, B505, which does not appear to bind any hCGβcf nor hLH in liquid phase assays.

FIG. 7 HLH and hLHβcf in serum and urine of the same patient. The blood levels of intact hLH (open circles) and hLHβcf (closed circles) are illustrated in the upper panel. It indicates that there is an insignificant amount of the hLHβcf detected in the blood. The lower panel illustrates the urinary values for hLH and hLHβcf in the urine for the same days of collection. The surge of hLH(day 0) and the surge of hLHβcf (1–2 days later) are detected in urine, but the peak of hLHβcf lags that of the intact hLH by 1–2 day, suggesting that the origin of urinary hLHβcf is the peripheral or renal metabolic processing of intact hLH.

DETAILED DESCRIPTION OF THE INVENTION

Figure 1:
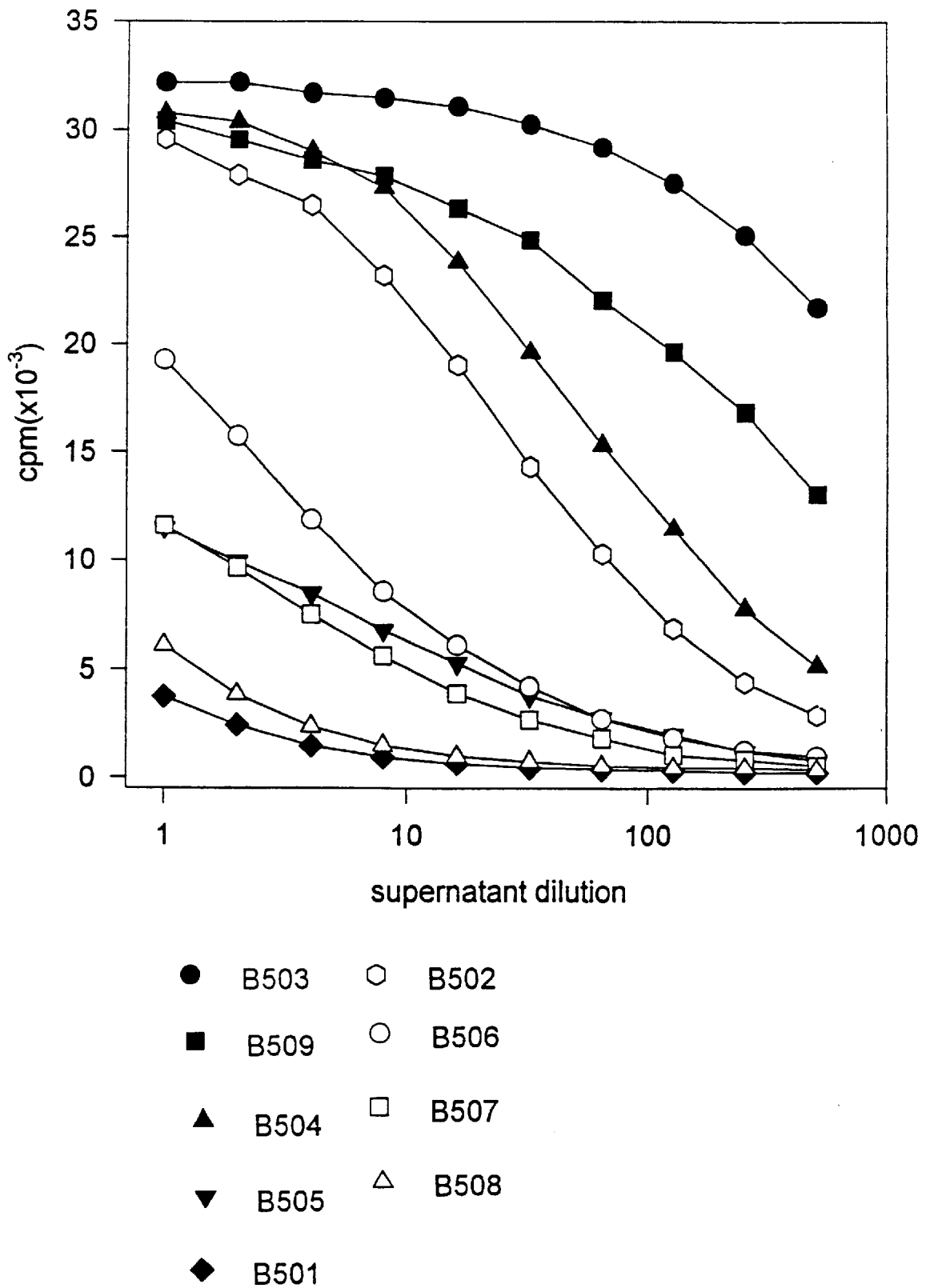
FIG. 1 Antibody dilution curves for the 9 hybridoma supernatants with $^{125}$I-hLHβcf in liquid phase RIA. Dilution of cell supernatant appears on the X-axis while the total counts of tracer bound appears on the Y-axis.

This invention provides an antibody which specifically binds to hLHβcf without cross-reacting with hLH, hLHβ or hCGβcf. In an embodiment, the monoclonal antibody is designated B505. In a further embodiment, the hybridoma cell line producing the monoclonal antibody B 505 is designated ATCC Accession No.HB-12000.

This hybridoma cell was deposited on Dec. 11, 1995 with the American Type Culture Collection (ATCC), 10801 University Boulevard Manassas, Va. 20110-2209 under the provision of the Budapest Treaty for the International Recognition of the Deposit of Microorganism for the Purposes of Patent Procedure. This hybridoma has been accorded with ATCC Accession No. 12000.

This invention also provides hLHβcf antibody which competitively inhibits the binding of the monoclonal antibody B505.

This invention provides a method for determining the amount of hLHβcf or hLHβcf-related molecule in a sample comprising steps of: (a) contacting the sample with an antibody which specifically binds to hLHβcf without cross-reacting with hLH, HLHβ or hCGβcf under condition permitting formation of a complex between the antibody and hLHβcf; and (b) determining the amount of complexes formed, thereby determining the amount of hLHβcf or hLHβcf-related molecule in the sample. In an embodiment, the antibody is produced by the hybridoma cell line accorded with ATCC Accession No.12000. In another embodiment, the antibody is labelled with a detectable marker. In a further embodiment, the antibody is radioactively labelled.

As the methodology of radioimmunoassay (RIA) is well known in this art, an ordinary skilled artisan can easily use this methodology for determining the amount of hLHβcf or hLHβcf-related molecule in a sample using the disclosed antibodies.

This invention provides a method for determining the amount of hLHβcf or hLHβcf-related molecule in a sample comprising steps of: (a) contacting at least one capturing antibody selected from a group consisting of B503, B504 and B509 with a solid matrix under conditions permitting binding of capturing antibody with the solid matrix; (b) contacting the bound matrix with the sample under conditions permitting binding of the antigen present in the sample with the capturing antibody; (c) separating the bound matrix and the sample; (d) contacting the separated bound matrix with an antibody which specifically binds to hLHβcf without cross reacting with hLH, hLHβ or hCGβcf; and (e) determining the amount of bound antibody on the bound matrix, thereby determining the amount of hLHβcf or hLHβcf-related molecule in the sample. In an embodiment, the antibody is B505. Methods for determining the amount of antibody bound to an antigen are well-known in the art. For example, the detecting or the secondary antibody may carry a detectable marker. A standard curve may be generated using known amounts of the tested antigen and the amount of signal generated by the marker.

This invention also provides monoclonal antibodies, B503, 504 and 509. This invention also provides hybridoma cell lines producing the monoclonal antibody B503, 504 and 509. These hybridoma cell lines were deposited on Dec. 11, 1995 with the American Type Culture Collection (ATCC), 12301 Parklawn Drive, Rockville, Md. 20852, U.S.S. under the provision of the Budapest Treaty for the International Recognition of the Deposit of Microorganism for the Purposes of Patent Procedure. These hybridoma have been accorded with ATCC Accession Nos.11999, 12001 and 12002 respectively.

In performing the above method, the separation of the bound matrix and the sample in step (c) may be carried out by: (i) removing of the sample from the matrix, and (ii) washing the bound matrix with an appropriate buffer. Alternatively, they may be separated by other methods known in the art.

This invention also provides methods for determining the amount of hLHβcf or hLHβcf-related molecule in a sample comprising steps of: (a) contacting a capturing antibody which specifically binds to hLHβcf without cross-reacting with hLH, hLHβ or hCGβcf with a solid matrix under conditions permitting binding of the antibody with the solid matrix; (b) contacting the bound matrix with the sample under conditions permitting binding of the antigen present in the sample with the bound capturing antibody; (c) separating the bound matrix and the sample; (d) contacting the separated bound matrix with at least one detecting antibody selected from a group consisting of B503, B504 and B509 under conditions permitting binding of antibody and antigen in the sample; and (e) determining the amount of bound antibody on the bound matrix, thereby determining the amount of hLHβcf or hLHβcf-related molecule in the sample.

In an embodiment, the antibody which specifically binds to hLHβcf without cross-reacting with hLH, hLHβ or hCGβcf is B505. In a further embodiment, the antibody is labelled with a detectable marker. In a still further embodiment, the detectable marker is a radioactive isotope, enzyme, dye or biotin. In a further embodiment, the radioactive isotope is $I^{125}$.

This invention also provides a method of detecting ovulation in a female subject comprising: (a) obtaining samples from the female subject; and (b) determining the amount of hLHβcf or hLHβcf-related molecule in the samples, the presence of a peak of hLHβcf or related molecule indicating the occurrence of ovulation.

This invention further provides the above method, wherein step (b) comprising: (i) contacting the sample with an antibody which specifically binds to hLHβcf without cross-reacting with hLH, hLHβ or hCGβcf under conditions permitting formation of complex between the antibody and hLHβcf; and (ii) determining the amount of the complex, thereby determining the amount of hLHβcf or related molecule in the samples.

This invention further provides the above-method, wherein the antibody is labelled with a detectable marker.

In an embodiment, the monoclonal antibodies of this invention are labelled with a detectable marker, for example, a radioactive isotope, enzyme, dye or biotin. In a further embodiment, the radioactive isotope is $I^{125}$.

In an embodiment of the above described method, the sample tested is a urine sample. In a separate embodiment, the sample is a blood sample.

This invention provides a method for reducing the amount of hLHβcf or related molecule in a sample comprising steps of: (a) contacting the sample with an antibody which specifically binds to hLHβcf without cross-reacting with hLH, hLHβ or hCGβcf under conditions permitting formation of complex between the antibody and hLHβcf; and (b) removing the complex formed, thereby reducing the amount of hLHβcf or hLHβcf related molecule in the sample.

This invention provides the above method, wherein the removing step comprising: (i) contacting the complex with protein A under conditions permitting formation of protein A with an antibody; and (ii) removing the complex formed, thereby the amount of hLHβcf or hLHβcf related molecule in the sample.

In an embodiment of this method, the complex is contacted with a secondary antibody under conditions permitting binding of the secondary antibody to the first antibody prior to step (i). In a separate embodiment of this method, the antibody is linked to a solid matrix.

This invention further provides samples with reduced amount of hLHβcf produced by the above-described methods.

As stated herein, samples include but not limited to urine sample and blood samples.

It is clear that all the methods described in this invention are applicable to hLHβcf-related molecules. Such molecules are defined as molecules capable of being recognized by the antibody which specifically binds to hLHβcf without cross-reacting with hLH, hLHβ or hCGβcf. Specifically, the hLHβcf-related molecules may be recognized by B505.

This invention will be better understood by reference to the Experimental Details which follow, but those skilled in the art will readily appreciate that the specific experiments detailed are only illustrative of the invention as described more fully in the claims which follow thereafter.

Experimental Details

Materials and Methods

Preparation of hLHβcf

The extraction of the hLHβcf from human pituitary extracts was reported earlier(Birken et al., 1993). Applicants prepared approximately 700 μg of hLHβcf from 8 g of starting human pituitary glycoprotein extract.

Other Hormones

HLH was obtained from two different sources. One preparation of hLH was a gift from Dr. Anne Stockell Hartree (Hartree, 1975). This preparation of hLH was completely intact by amino acid sequence analysis. A second preparation of hLH (AFP 8270B), as well as one of hLH beta (AFP 3282B), used in these studies were obtained from the National Pituitary Agency. Which preparation was used in various studies is indicated within the text. The isolation of hCGβcf was described earlier (Birken, et al., 1988). $^{125}$I-hLH was obtained from Diagnostics Products Corporation.

Iodination of hLHβcf and hCGβcf

HLHβcf and hCGβcf were iodinated using Iodogen (Pierce Chemical Co., Rockford, Ill.) according to manufacturer's instructions.

Purification and Iodination of Monoclonal Antibodies.

Immunoglobulins were purified from ascites by the Protein A Monoclonal Antibody Purification System (Bio-Rad, Richmond, Calif.). The protein concentration of pure antibodies was determined by amino acid analysis. Purification of mABs was checked by a PAGE in the presence of SDS according to Laemmli (Laemmli, 1953). Pure antibodies were labeled with $^{125}$I by chloramine T-method (Hunter and Greenwood, 1962). Not less then 70% of the radioactivity was able to bind specifically hLHβcf.

Immunization of Mice

Balb/c mice were immunized twice subcutaneously with 4–6 μg of hLHβcf per each animal in complete (first immunization) or incomplete (second immunization) Freund's adjuvant. The second immunization was carried out on day 14 after the first immunization. On days 21 and 28 the mice were immunized intraperitoneally (ip) with 4 μg of antigen per animal. On the day 35 blood was taken and sera were tested for antibodies. Mice with high antibody response were boosted with 6 μg hLHβcf iv and after 3 days used for fusion.

Cell Fusion

Spleen cells from immunized mice were fused with cells of myeloma line X63-Ag8.653 3 days after the booster injection according to the method of Kohler and Milstein (Kohler and Milstein, 1975). The splenocyte to myeloma cell ratio was 4:1 or 5:1. Polyethylene glycol 4000 (Sigma, St. Louis, Mo.) was used as fusing reagent. After fusion, cells were distributed in 6 microtitration plates on mouse peritoneal feeder cells and cultured for one week in HAT-selection RPMI 1640 or DMEM media containing 20% FCS. One half of the medium was replaced every 3 days. One week after fusion, HAT-medium was changed for HT. On day 12–14 post fusion, culture supernatants (100 ml) from the wells with cell clones were screened for the presence of antibodies to hLHβcf using liquid phase RIA. Positive selected cells were cloned at least two times by limiting dilutions on mouse peritoneal feeder cells. Subclones were injected intra peritoneally into Balb/c mice (0.5–×10$^6$ cells/mouse) and the ascites produced were used as source of mABs. Hybridoma cells were stored in liquid nitrogen in FCS containing 10% DMSO.

Screening of Primary Clones

Primary screening was carried out in liquid phase RIA with $^{125}$I-hLHβcf. The liquid phase RIA procedure was described earlier (Birken et al., 1980). In brief, the binding buffer consisted of PBS supplemented with 0.1% BSA and 0.02% sodium azide. 150 ml solution containing 30,000–40,000 cpm $^{125}$I-hLHβcf was added to 100 ml culture supernatant diluted 2.5:1 with PBS. 50 ml of 8% normal mouse serum was also added. This solution was incubated for 1 h at 37 C. and after that overnight at 4 C. Then 500 ml of a 2.5% goat anti-mouse serum was added and mixture was incubated for 1 h at 37 C. and for 2 h at room temperature. The precipitate containing bound radioactive hLHβcf was separated by centrifugation and counted in a gamma counter. Supernatants of positive clones were tested in the same kind of assay to check cross-reactivity with $^{125}$I-hCGβcf and $^{125}$I-hLH. Immune serum as a positive control was used.

Competitive Liquid Phase RIA

Competitive liquid phase radioimmunoassays were conducted as follows: Cell supernatants were used in those dilutions at which approximately 40% of maximum antibody binding occurred in the absence of unlabeled hormones. The following reagents were added to each 12×75 mm polystyrene tube: 100 ml diluted supernatant, 30,000–40,000 cpm of $^{125}$I-hLHβcf in 300 ml binding buffer (PBS, pH 7.2 with 0.1% BSA), 100 ml competitor solution and 100 ml 8% normal mouse serum. After incubation for 1 h at 37 C. and overnight at 4 C., 1 ml 2.5% goat anti-mouse serum was added as in the primary screening. The cross reactivity of different competitors was calculated by the PC version of the program Allfit written by DeLean et al. (De Lean et. al., 1992). Likewise, affinity constants were calculated by homologous competitive displacement assays using the PC version of the program Ligand by Munson (Munson and Rodbard, 1980).

Competitive Solid Phase RIA

Each antibody was adsorbed onto the wells (100 ml per well) of microtiter plates (Immulon II, Dynatech, Chantilly, Va.) by incubating a solution of the antibody (B503-2 μg/ml, B504-1 μg/ml, B505-5 μg/ml, B509-5 μg/ml) in 0.2 M bicarbonate, pH 9.6 overnight at 4 C. The coating antibody solution was aspirated, the plates were washed with PBS and blocked with 2% solution of BSA in PBS for 3 h at room temperature. The blocking solution was removed, the plates were washed with PBS and 100 ml of binding mixture was added to each well. The binding mixture, which contained $^{125}$I-hLHβcf and dilutions of antibodies in PBS with 0.1% bovine gamma globulin, was preincubated at 37 C. for 1 h. After an incubation for 2 h at room temperature and overnight at 4 C. the solution was aspirated, the plates were washed with PBS and bound radioactivity was counted. Results were presented as percentages of $^{125}$I-hLHβcf binding in the absence of competitor.

IRMA

Applicants' methodology for the construction and validation of Immunometric assays has been fully described (O'Connor et al., 1988). Briefly, the specificity of the antibody pairs and their capacity for simultaneous binding to antigen are determined as follows. The analytes tested for potential cross reaction with the hLHβcf monoclonal antibodies included hCGβcf, hLH (AFP 8270B), hLH free β subunit (AFP 3282B), intact hCG (CR 127) and hCG free β subunit (CR129). The degree of cross reaction was anticipated from a knowledge of antibody specificity in liquid phase RIA. The range of the β core LH standards was 3.9 to 1000 fmol/ml. The range of cross reactants encompassed 39 to 278000 fmol/ml, depending on the analyte.

The capture antibody (marked by a single asterisk in Table 2) was adsorbed onto the wells of microtiter plates by incubating a 20 μg/ml solution of the antibody in coating buffer (0.2 M bicarbonate, pH 9.5) overnight at 4 C. The coating antibody solution was aspirated, the plates washed (wash solution 0.9% NaC1, 0.05% Tween 20) and blocked with a 1% solution of BSA in water. Following incubation with the BSA solution (minimum 3 hours at room temperature) the blocking solution was removed, the wells again washed and 200 ml/well of the appropriate hLHβcf standards or potential cross-reacting molecules were added in phosphate buffer B (0.05 M phosphate with 0.1% bovine gamma globulin and 0.1% NaN$_3$). After overnight incubation at 4 C., the plates were again aspirated and washed. The 200 ml (50,000 cpm )of appropriate $^{125}$I-labeled detection antibody (listed with double asterisks in Table 2) was added to the wells which were again incubated for 24 h at 4 C. The tracer was aspirated, the plates washed with water, the individual well placed in glass tubes and the radioactivity determined in a Packard Cobra gamma counter. Doses were determined by interpolation from a smoothed spline transformation of the data points.

In addition to hLHβcf assays, three other assays, described earlier, were used for hLH and hLHβ (Krichevsky et. al., 1994) and for the hCGβcf (Krichevsky et al., 1991).

For the assay of urinary hLH and its metabolic forms, the following antibody pairs were employed: For intact hLH, B406*–A201**; for the hLH free beta subunit, B408*–B409**; and for the hLHβcf B505*–B503**. Prior to assay, the urines are thawed, the pH is adjusted with 1.0 M Tris (pH 9.5), 50 μl/ml urine, and aliquoted (200 μl/well) into 96 well microtiter plates which had been previously coated with capture antibody and blocked with BSA. A serially diluted standard curve of the appropriate analyte (intact hLH, hLH free beta subunit or hLH beta core fragment) is added in buffer B to the wells and the plate is incubated overnight at 4 C. The assay is performed from that point identically to that described for antibody characterization.

Steroid Glucuronide Enzyme Immunoassay

The solid phase ELISAs for estrone 3-glucuronide and pregnanediol 3-glucuronide were performed with reagents provided by Drs. Bill Lasley and George Stobenfield of the University of California, Davis. The assay has been fully described previously (Krichevsky et al., 1994).

sive homology among these three hormone fragments as well as the scarcity of the hLHβcf prompted us to employ radiolabeled molecules for initial screening of the supernates of cells during the clonal selection process. Splenocytes from animals displaying high serum titers to the radiolabeled hLHβcf were fused with high efficiency (75–85%). Three fusions were successful in producing a large number of cell lines which bound radiolabeled hLHβcf. A total of 112 positive clones was produced. Each well supernate was ranked in terms of binding specificity by assigning the supernate from wells which bound the highest amounts of radiolabeled hLHβcf as 100%. The same procedure was used to set the maximal binding of radiolabeled of hLH and hCGβcf. Assuming that each well supernate contained about the same quantity of antibody, the relative percentage of binding of each radiolabeled protein was calculated. Examination of the data indicated that 606% of positive clones (clones with cell supernates that bound hLHβcf) recognized all three radiolabeled proteins, 12% bound both hLHβcf and hCGβcf, 8% recognized hLHβcf and hLH, and 20% of the clones appeared fairly specific to the hLHβcf. Those clones which demonstrated the best growing characteristics were subcloned at least twice and sufficient cell supernatants of each clone was produced for further characterization studies. Titration binding curves of supernatants from clones of interest were performed in liquid phase RIA using. $^{125}$I-hLHβcf as a tracer (FIG. 1). This study permits rapid comparisons of the relative antibody affinity of each of the clones (Heyningen et al., 1983). It was assumed that the concentration of antibodies in each supernatant varied only slightly. The titration study shows that mABs B509, B503 and B504 have the highest affinities. Although antibody B505 has a lower affinity than these other antibodies, it has the best specificity for the hLHβcf and, thus, it was also selected for further study.

Four antibodies to the hLHβcf, B505, B509, B504, and B503 were characterized for relative specificities and sensitivities in a series of competition curves using radiolabeled hLHβcf and unlabeled hLHβcf, hCGβcf and hLH as competitors. The results of these studies are summarized in FIG. 2 and Table 1.

TABLE 1

Characteristics of mABS to hLHβcf

| Antibody | Isotype | $K_a$, M$^{-1}$, (cv, %) | ED+/−SE, hLHβcf, pmole/ml | ED+/−SE, hLH, pmole/ml | ED+/−SE, hCGβcf, pmole/ml | Cross-reactivity**, hLH, % | Cross-reactivity** hCGβcf, % |
|---|---|---|---|---|---|---|---|
| B505 | G1 | 3.01 × 10$^8$ (86) | 6.49+/−0.326 | >>80 | >>320 | nd | nd |
| B509 | G1 | 1.37 × 10$^{10}$ (9) | 0.228+/−0.0089 | 6.135+/−0.72 | >140 | 3.72 | <0.16 |
| B504 | G1 | 2.06 × 10$^{10}$ (10) | 0.205+/−0.011 | 0.157+/−0.011 | 1.385+/−0.088 | 130 | 14 |
| B503 | G2a | 1.31 × 10$^{10}$ (11) | 0.335+/−0.0097 | 0.953+/−0.035 | 0.414+/−0.013 | 35 | 80.9 |

*ED-concentration of hormones needed to inhibit 50% of 125-iodo-hLHβcf binding to various mABs in liquid phase RIA; **-was determined in liquid phase RIA; SE-standard error; nd-not determined Isotyping of mABs Isotypes of mABs were determined using Mouse Monoclonal Sub-isotyping Kit (HyClone, Logan, Utah) according to the manufacturer's instruction except that the plate was coated with hLHβcf (0.1 mg/well) instead of rabbit anti-mouse immunoglobulins.

Experimental Result

In order to choose antibodies specific to the hLHβcf, applicants selected for high affinity binding to the hLHβcf, which was the immunogen, and also, for very low or no binding to hCGβcf and to hLH and free hLHβ. The exten- These antibodies were characterized (Table 1) in terms of their isotype, affinity constants, and cross-reactivity. FIG. 2, which presents liquid phase competition studies, shows that all four of these antibodies are different in their relative binding characteristics. Antibody B509 is slightly cross-reactive with hLH and hCGβcf (FIG. 2A); Antibody B504 binds hLH and hLHβcf approximately equally (FIG. 2C); Antibody B503 binds all three competitors in a very similar fashion (FIG. 2D). Antibody B505 binds hLHβcf quite specifically (FIG. 2B). Although liquid phase cross-reactivities are not paralleled precisely in the two-site format solid phase assay, the liquid phase data indicates that these four antibodies are different and may have different binding sites making them amenable to two-site assay development. The quantitative analysis of sensitivities and cross reactivities for these four antibodies are summarized in Table 1. Three antibodies (B503, B504 and B509) displayed high affinities in the $10^{10}$ M$^{-1}$ range. Antibody B505 was in the range of $10^8$ M$^{-1}$. The cross-reactivity of antibody B505 with the hCGβcf and with hLH were too low to measure.

Table 2 details the characteristics of two-site IRMAs developed using the new antibodies described in this report. The four monoclonal antibodies described in this report functioned in combination with each other to produce excellent immunometric assays for hLH-beta core fragment. Analytes tested for cross reactivity in these systems included hCG beta core fragment, hLH, hLH free beta subunit, hCG, and hCG free beta subunit.

Figure 3A:
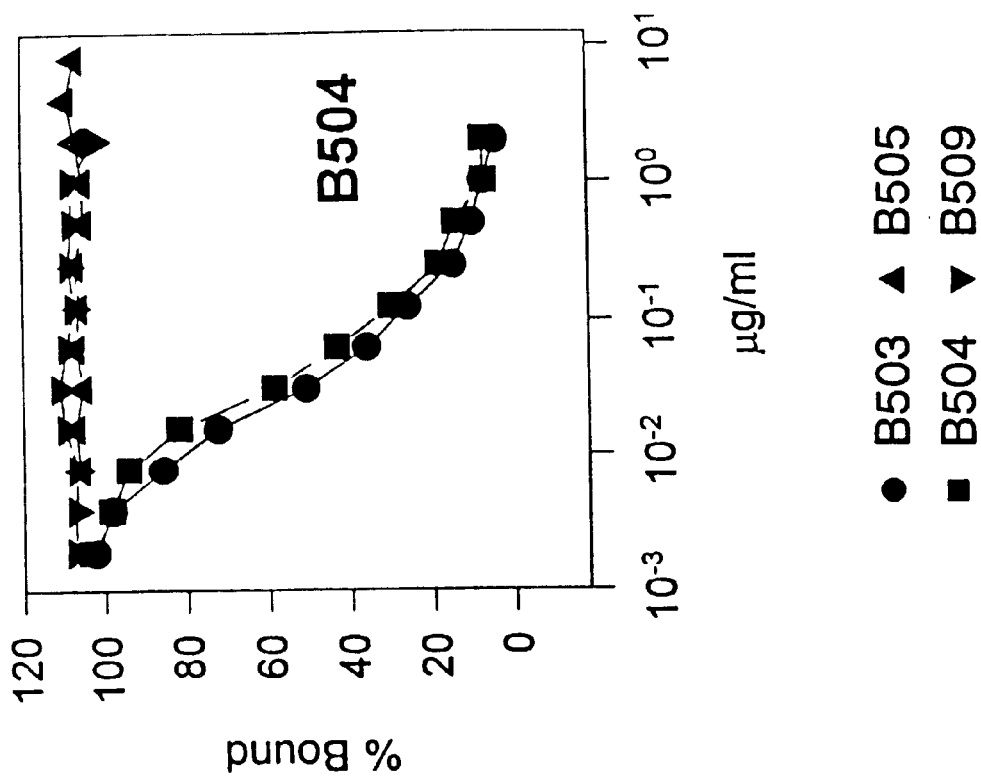
FIG. 3 Competitive curves of the binding of mABs in solution with mABs immobilized on the plate for binding to $^{125}$I-hLHβcf in solid phase RIA. Panel C shows the enhancement of binding of tracer when either antibodies B503 or B504 is added to B505 immobilized on the plate. This enhancement is due to the cooperativity in formation of "a circular complex" (Ehrlich et al., 1982) and has led to a two-site assay of extraordinary sensitivity with an extended measurement range.
Figure 3B:
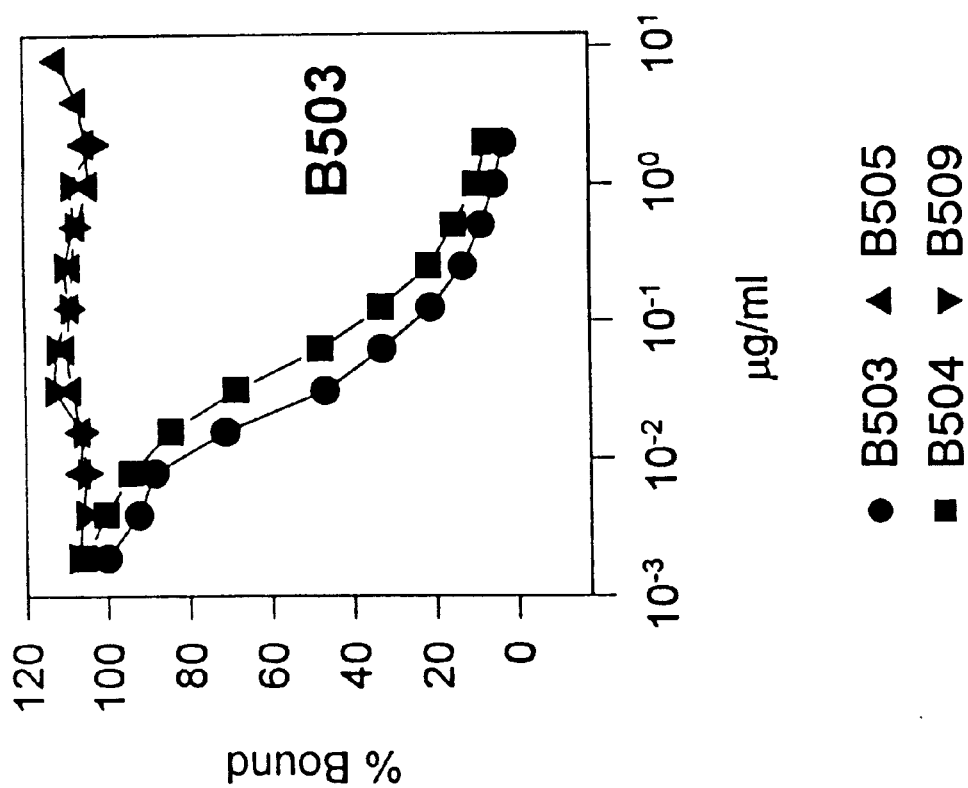
Figure 4A:
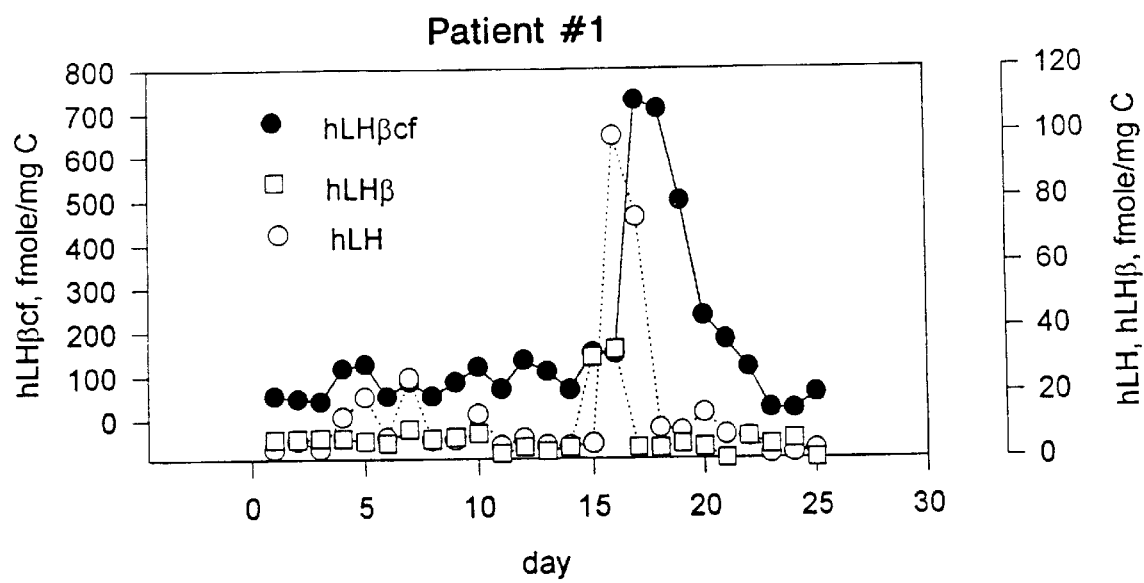
FIG. 4 The hormonal profiles of two ovulatory menstrual cycles from normal women (patient #1 and #2). All values have been normalized to creatinine. Panels A in both subjects show values for intact hLH, hLHβ and hLHβcf in urine. Panels B provide data on two urinary steroid metabolites, estrone-3-glucuronide and pregnanediol-3-glucuronide. Note that in both subjects the concentrations of hLHβcf substantially exceed that of the intact hLH and hLHβ and that its maximum excretion appears to lag that of hLH and hLHβ by one day.
Figure 4B:
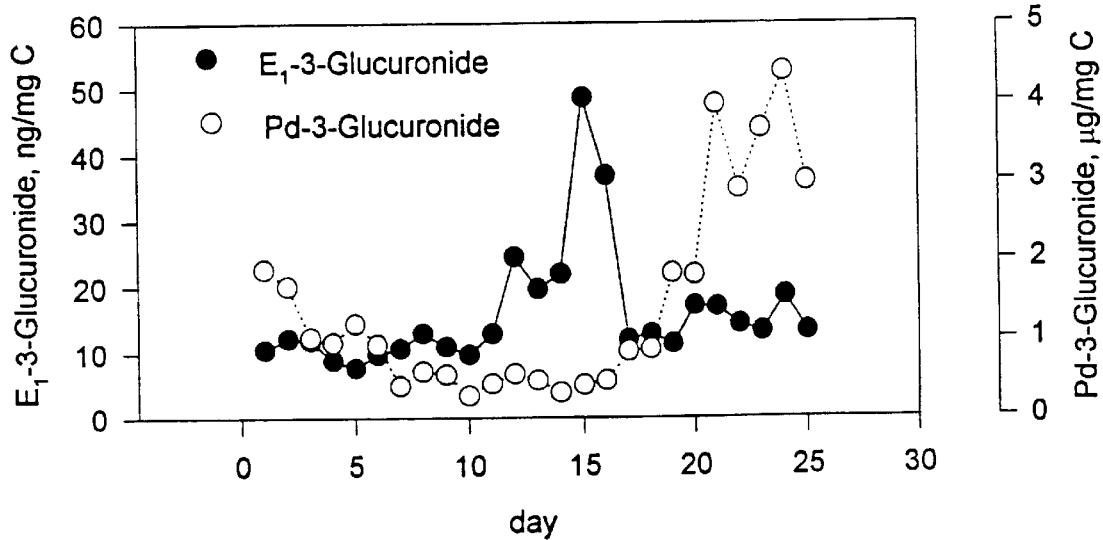
Figure 4C:
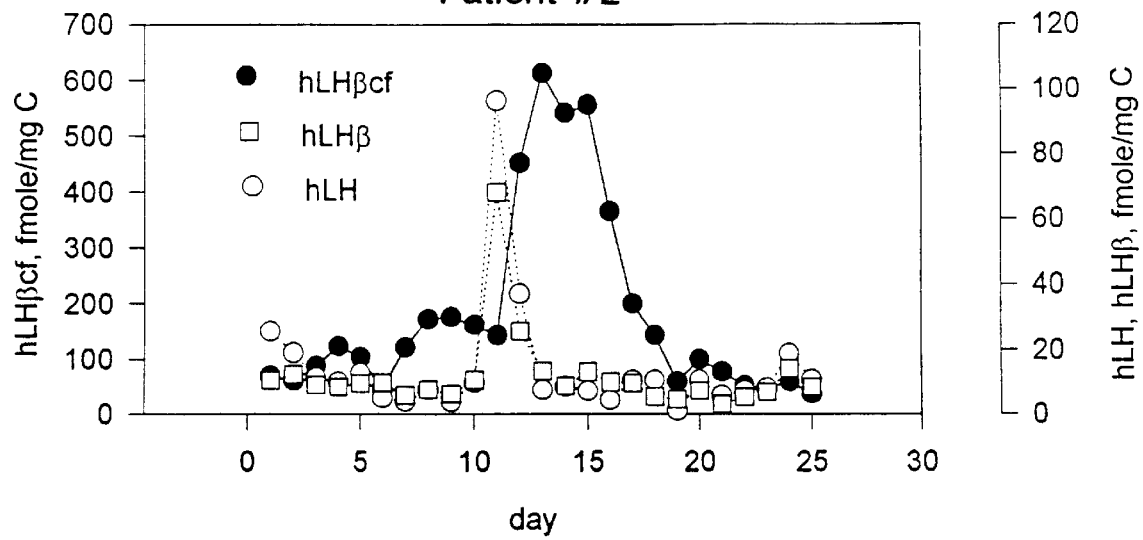
Figure 4D:
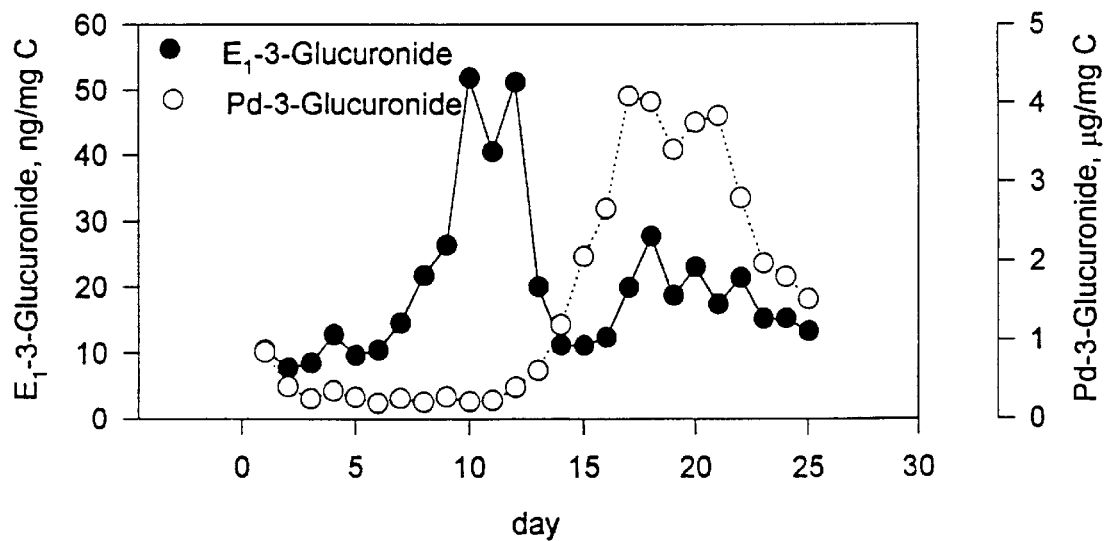
Figure 5:
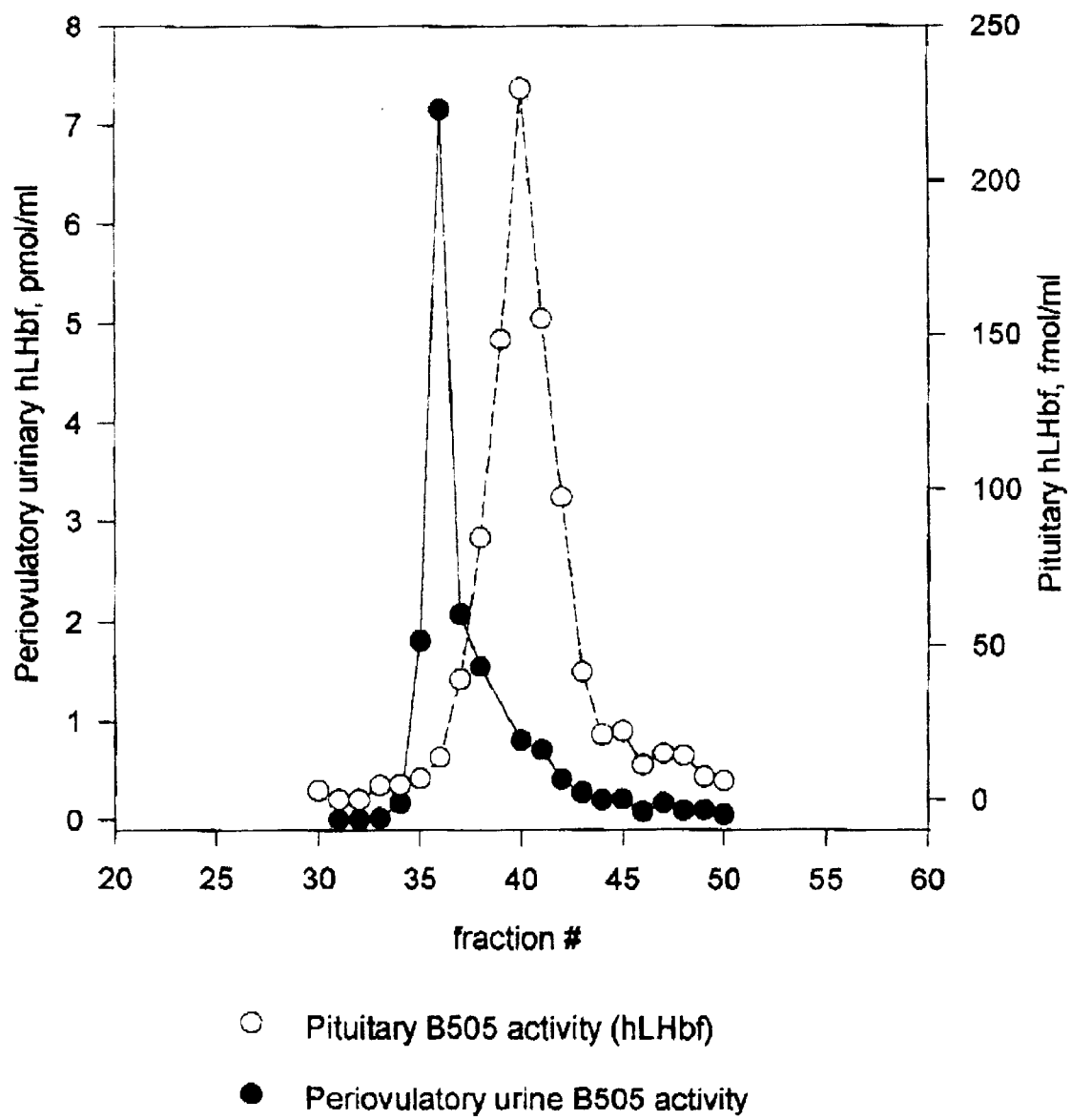
FIG. 5 HPLC elution positions of the pituitary and urinary hLHβcf. The open circles denote the elution position of hLHβcf derived from the pituitary. The closed circles denote the elution position of hLHβcf—partially purified from urine. The difference in elution position denotes a structural difference (probably carbohydrate differences) between the two forms. The column separates molecules on the basis of hydrophobicity. Both the urinary molecule and the pituitary derived molecule exhibit immunoreactivity with B505 as well as B503, B504, and B509.
Figure 6A:
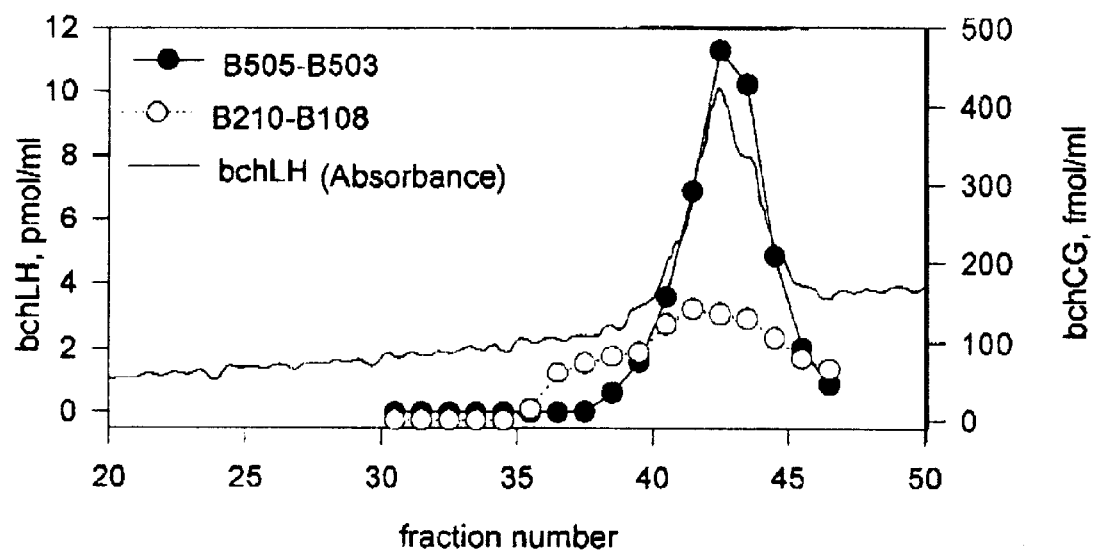
FIG. 6 Study of rechromatography of the pituitary hLHβcf on reverse phase HPLC in order to calculate true cross-reactivity of pituitary hLHβcf in the assay which has been used for measurement of urinary hCGβcf (B210–B108). The concentration of pituitary hLHβcf as well as the concentration of hCGβcf were measured in each of the same column fractions of a single separation. The concentration of pituitary hLHβcf was determined by B505–B503 assay and appears on the left Y-axis while the concentration measured by the hCGβcf assay appears on the right axis as determined by the B210–B108 assay using urinary hCG fragment standard. The latter assay is presumed to measure true cross-reactivity of pure pituitary hLHβcf within fractions 40–45 while 37–39 may represent the slight contamination with pituitary hCGβ which appears prior to pituitary hLHβcf in this system (Hoermann et al., 1995). Note that the left axis of panel A is pmole/ml while the right axis, representing the hCGβcf, is in fmol/ml showing that the cross reaction of the hCGβcf (B210–B108) assay with the hCGβcf is very low as is the contamination with the pituitary hCGβcf. Lower panel B shows the position of urinary hCGβcf on this column system which presumably elutes in a similar fashion to authentic pituitary hCGβcf (Hoermann et al., 1995).
Figure 6B:
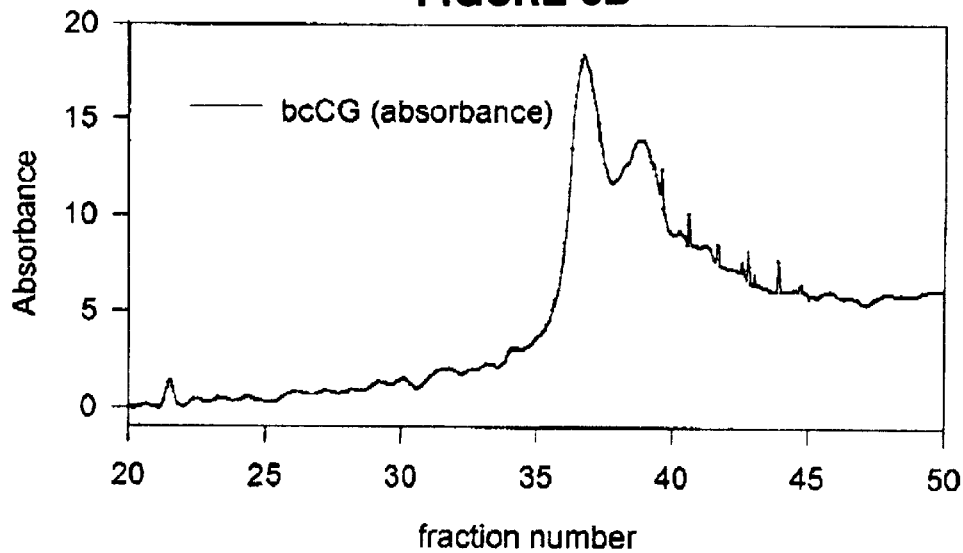

A detailed analysis of the simultaneous interactions of two antibodies with the hLHβcf was conducted to distinguish those antibodies which cannot bind simultaneously from those that bind at the same time. Enhanced simultaneous binding is especially desirable. The study of the interactions of the four hLHβcf antibodies was accomplished using iodinated hLHβcf, one immobilized solid phase antibody and one liquid phase antibody (Gomez and Retegui, 1994). These findings are illustrated in FIG. 3. The results of these studies indicated that antibodies B503 and B504 competed for antigen and were clearly directed to the same antibody binding site. With immobilized B505, all three other anti-hLHβcf antibodies demonstrated binding synergism or cooperativity. The binding of labeled hLHβcf to immobilized B505 more than doubles in the presence of B503 and B504 (FIG. 3C). The effect was most pronounced with mABs B504 and B503, less so for B509, which appears to share an overlapping site with B505. Antibodies B505 and

TABLE 2

Characterization of immunoradiometric assays for hLHβcf

| Assay | Bmax, % | LDD, fmol/ml | Cross-reactivity with analyte | | | | | |
|---|---|---|---|---|---|---|---|---|
| | | | hLHβcf, % | hCGβcf, % | hLH, % | hLHβ, % | hCG, % | hCGb, % |
| B505*-B503** | 83 | 1.3 | 100 | 0.1 | 1.1 | 1.3 | 0.2 | 1.4 |
| B505*-B504** | 71 | <<4 | 100 | 0.05 | 1.3 | 0.05 | 0.43 | 2.6 |
| B505*-B509** | 39 | 4 | 100 | 0 | 0 | 0 | 0 | 0 |
| B509*-B503** | 86 | <4 | 100 | 6 | 6 | 1 | 0.3 | 3 |
| B509*-B504** | 90 | <<4 | 100 | 5.8 | 6.5 | 1.1 | 6.4 | 3.1 |
| B509*-B505** | 3 | 125 | <1 | <1 | <1 | <1 | <1 | <1 |
| B201*-B108** | 50 | 0.7 | 2 | 100 | <1 | <1 | 1 | <1 |

*-Antibody immobilized on the solid phase, **-antibody labeled with $^{125}$I, LDD-lowest detectable dose, Bmax-max binding of total count The most useful assays were provided by employing either B509 or B505 as capture and B503 or B504 for detection. In all of the above combinations, a sensitivity of less than four fmoles/ml was realized (sensitivity defined as NSB+3SD). The assay which provided the best combination of sensitivity and specificity proved to be the B505 capture, B503 detection system. The sensitivity of this configuration was about one fmole/ml and the cross reaction with all of the tested analytes was under 2%. Cross-reaction with the hCG beta core fragment was less than 0.1% while cross-reaction with hLH was about 1%. However, even better specificity is afforded by the B505*-B509** combination, in which it was not possible to detect any cross-reactivity with the other analytes over the range tested. This configuration has the disadvantages of both decreased sensitivity (4 fmol/ml vs about 1 fmol/ml for B505*-B503**) and a diminished B-max relative to the other assays, probably reflecting partial overlap of the two epitopes. Nevertheless, in those instances where extreme sensitivity is not required, but in which any cross-reacting analytes are present, then the B505*-B509** configuration is certainly an acceptable alternative. The last row of Table 2 indicates the cross-reactivity of applicants' previously developed two-site immunoassay to the hCGβcf (B210*-B108**) with pituitary hLHβcf to be approximately 2%.

B509 bind to different sites on the hLHβcf than do B503 and B504. No other antibody combination other than those with immobilized B505 display binding cooperativity. Cooperativity between B505 and B503 detection has permitted the construction of a highly sensitive (1 fmol/ml) immunometric assay for hLHβcf having a wide dynamic range (0–1000 fmol/ml).

MAB B505 performs only marginally or not at all as a detection antibody when labeled with $^{125}$I. This inhibition applies whether the iodination is performed by either Chloramine T or the Iodogen techniques. This suggests that perhaps a tyrosine(s) in or near the binding site is affected by iodine substitution.

The potential clinical utility of these assays is illustrated by the menstrual cycle profiles of 7 normally ovulating women two of whom are presented in FIG. 4. In these cycles the peak excretion of hLHβcf lags that of the intact hLH at least by one day. The values for hLHβcf in these subjects exceed those of hLH and hLHβ (both of which peaked the same day) by 6–7 fold (FIG. 4). One patient exhibited a rise in hLHβ immunoreactivity one day prior to the hLH surge and this patient appears in FIG. 4. Measurement of the urinary steroid metabolites estrone-3-glucuronide and pregnanediol-3-glucuronide confirmed that the ovulation had occurred in these cycles (FIG. 4, Panel B). There appears to be a basal pulsatile concentration of the hLHβcf in the urine.

Experimental Discussion

Although a variety of hLH antibodies have been reported in the literature during the past several years (Krichevsky et al., 1994, Alonso-Whipple et al., 1988, Odell and Griffin, 1987), this is the first report of antibodies and two-site assays specific to the hLHβcf. In fact, applicants have only recently confirmed the existence of the hLHβcf by structural studies of this core material isolated from a pituitary extract (Birken et al., 1993). These new antibodies and the IRMA systems described in this report should provide important reagents to determine the pattern of excretion of this metabolite into urine. A molecule of the size and immunochemical properties of this metabolite appears to be present during the normal ovulatory cycle after the hLH surge (Neven et al., 1993) and is present in postmenopausal women (Iles et al., 1992 ). Those investigators used antibodies developed to the hCGβcf which they hypothesized to cross-react with a putative hLHβcf in urine. However, without antibodies individually specific for only one of the β core metabolites, it is not possible to distinguish hLHβcf from hCGβcf. The pattern of occurrence of such gonadotropin metabolites may provide important clinical information related to the health of a patient. For example, although the hCGβcf has been identified as a marker molecule associated with a variety of malignancies (O'Connor et al., 1988; Cole et al., 1988a, 1988b, 1990; O'Connor et al., 1994), its value as such a marker in postmenopausal women has been limited by the presence of an immunochemically cross-reacting molecule of similar size (Iles et al., 1992). This molecule is likely to be derived from hLH and is probably the hLHβcf. Development of the specific two-site assays described in this report should make it possible to accurately measure the concentration of hLHβcf in the presence of the hCGβcf as well as high levels of hLH in urine. These assays may have a direct application for studies of markers related to menopause, the ovulatory cycle, as well as to distinguish normal postmenopausal women from those with cancers.

Since purified hLHβcf was scarce, antigen-conserving techniques were used to select the desired antibodies. Although applicants wished to measure hLHβ metabolites in urine, applicants decided to pursue development of antibodies to a pituitary form of the hLHβcf since applicants had already isolated this material in a highly purified form. Applicants had not been able to isolate hCG-core fragment cross-reactive material directly from postmenopausal urine (Birken et al., 1993) but assumed it was a molecule derived from hLH based on the studies of Iles (Iles et al., 1992) and applicants' own work. The supply of pituitary hLHβcf was quite limited since its yield was only about 100 μg/g of crude pituitary extract. There were a number of considerations in selection of antibodies to this molecule. First, it was a low abundance protein within the pituitary extract. Therefore, the screening of antibody-producing cell supernates was done exclusively by radiolabeled protein because of the low supply of hLHβcf and the need to conserve protein for competition experiments later on. Secondly, since the structures of the hCG and hLHβcfs were very similar, it was likely to prove difficult to select antibodies which could clearly distinguish between the two molecules. Third, it was also necessary to select against binding to hLH and hLHβ since both are present in postmenopausal urine, as well as at the mid-cycle hLH surge in ovulating women, and their cross-reactions would complicate measurement of the hLHβcf. Fourth, it was necessary to select antibodies of medium to high affinity in order to be able to measure low levels of the hLHβcf in urine. Fifth, it was also necessary to select a set of antibodies which could be used in two-site measurement of the hLHβcf. The latter requirement made it necessary to develop a variety of antibodies to the hLHβcf.

The strategy used to select the diverse antibodies needed for development of the appropriate two-site assay was screening candidate antibody-secreting cells with three radiolabeled tracers: hLHβcf, hCGβcf and hLH. The resulting titration patterns from three fusions permitted selection of four cell lines secreting the appropriate antibodies. Liquid phase assay studies indicated that B505 was specific for hLHβcf (i.e. displayed no detectable cross-reaction with either the hCGβcf or hLH at the concentrations used) Antibody B509 was nearly equally specific for the hLHβcf versus the hCG fragment but displayed binding (3.72% in competitive liquid phase RIA) with hLH (Table 1). Two other antibodies bound all three proteins and proved excellent candidates for the second antibody in a two-site assay. Indeed, a two-site assay using B505 as capture and B503 as detection antibody was developed and displayed approximately 1% cross-reaction with hLH and hLHβ and 0.1% cross-reaction with the hCGβcf. Examination of the Table 2 indicates that this is the most satisfactory combination of antibodies for use in postmenopausal urine measurements, as well as measurements during the ovulatory cycle. Using liquid phase assays, it was found that the sensitivity of antibody B505 was only 7% (by ED50 calculations) that of B509 for the hLHβcf (Table 1). Yet, when two-site assays were developed separately for both antibodies, it was found that both exhibited the same sensitivity of less than 4 fmol/ml. This detection level sensitivity has proved to be more than adequate for the clinical measurements which applicants intend to perform. The solid-phase format resulted in a significant increase in antibody sensitivity in this case. The reason for the increase in sensitivity of B505 in solid phase assays is due to the cooperativity effect between B505 and B503 or B504. This effect arises from the formation of "a circular complex" of antibodies binding sites when the antibodies are positioned at appropriate distances from each other on the surface of a ligand, and is known to result in a much higher affinity than that of either antibody alone (Ehrlich et al., 1982). The affinity increases without any compromise of the excellent specificity of B505. This increase in affinity is very clearly shown in Table 2 and in FIG. 3.

The finding that the hLHβcf displays a unique epitope, which is not present on the hCGβcf nor on the hLH beta subunit, was surprising since the two fragments are very similar in primary sequence. The difference presumably lies within a variation of the structures of the two core fragments. Although the hLHβcf was isolated from a pituitary extract, the resultant antibodies detect this material in the urine of a normal cycling woman coincident with and then peaking a day or more after the hLH peak. This delay may result from metabolic processing of hLH within a peripheral compartment followed by the delayed release of fragments into urine. Studies by conducted by Dr. Nisula and colleagues by injection of hCG, hCGβ subunit and hCGβ core fragment into human volunteers as well as into animals showed that only 8% of injected hCG beta core fragment appears in the urine while 22% of injected hCG and 0.7% of hCGβ subunit enter the urine (Wehmann et al., 1989, Wehman and Nisula, 1981). The remainder of the molecules are taken-up by liver, ovary and kidney tissues and disposed of by routes other than urine. This group showed that after infusion of the hCG beta core fragment, its excretion into urine persists for as long as 7 days and they hypothesize uptake by renal parenchymal cells and slow re-excretion into urine (Wehmann et al., 1989). Such an uptake and re-excretion mechanism may explain the delay in appearance of the hLHβcf in urine after the hLH surge. Although the uptake and processing of hCG into hCGβcf is thought to occur within the kidney, it is not yet known where hLHβcf may be taken up and processed since the molecule is present within the pituitary and may be present in the circulation at higher levels than those very low levels observed for the hCGβcf. Further insight into the origin and clearance rate of the hLHβcf await optimization of serum and plasma assays and the ensuing clinical studies.

Iles et al. (Iles et al., 1992), Neven et al. (Neven et al., 1993) as well as the applicants (unpublished observations) have observed a periovulatory signal in the hCGβcf assay when menstrual cycle hormone profiles are examined. Immunological evidence has indicated that this signal is due in part to cross-reaction with an hLH associated molecule, but that conclusion was based on assays whose cross-reaction with hLHβcf was unknown. The appearance of substantial quantities of immunoassayable hLHβcf, as assessed by applicants' specific hLHβcf assay, in the hormone profile of normally cycling women, suggest this is in fact the case. The basal pulsatile concentration of the hLHβcf during the follicular phase in these cycling women probably reflects the metabolic processing of the normal circulating pulsatile hLH in blood during this time period. Conclusive evidence of the nature of these molecules awaits their isolation and structural determination. Applicants do not know as yet if the structure of this hLHβ core fragment present a mid-cycle in urine is identical to that isolated from pituitary although they share at least one unique epitope. Likewise, the structure of the hLHβ core in postmenopausal urine also remains to be defined. However, applicants report here a quantitative immunoassay for urinary hLHβcf using pituitary hLHβcf as standard allowing expression in molar units. Applicants have found that applicants' current hCGβcf assay cross-react with the hLHβcf 2% on a molar basis.

There are numerous reports in the literature that hLH exists as a variety of isoforms in the circulation and that many monoclonal antibodies fail to recognize some of these forms and produce erroneous measurement results (Petterson et al., 1991,1992; Stanton et al., 1993; Martin-Du-Pan et al., 1994). In fact, some hLH serum assays indicated the absence of hLH in a patient while other assays show normal levels Petterson et al., 1991). An analogous measurement problem is probably even more serious in urine since more degraded hLH molecules are likely to be present. As is the case for hCG, hLH appears to be metabolized to a beta subunit fragment of similar structure to the hCG beta core fragment upon passage into urine.

An additional potential application for these novel measuring systems may be in cancer diagnostics as described in the introduction. The hCGβcf has proven useful as a marker of gynecological cancer (Cole et al. 1988a, 1988b, 1990; O'Connor et al., 1988). Its usefulness is compromised by the simultaneous presence of an immunologically interfering substance in urine, especially postmenopausal women (Iles et al., 1992). It may be possible to use one of the hLHβcf antibodies as a scavenger for the hLH cross-reacting materials to reduce the threshold background so that the hCGβcf assays may be more useful for cancer detection and monitoring of cancer therapy.

The availability of these new hLHβcf antibodies now makes possible the conduct of clinical studies of this hLH metabolite in the urine of patients. These new immunometric assays provide the tools to study the relationship of the presence of this metabolite as compared to the analogous metabolite of hCG as indicative of health or disease. The extremely sensitive IRMA system for measurement of hLHβcf will be applied to the study of this excreted hLH metabolite in the urine of normal cycling women, infertility patients and as a possible marker of the onset of menopause.

References

Alonso-Whipple C, Couet M L, Doss R, Koziarz J, Ogungo E A, Crowley J W D 1988 Endocrinology 123:1854–1860

Birken S, Chen Y, Gawinowicz M A, Agosto G M, Canfield R E, and Hartree A S 1993 Endocrinology 133:985–989

Birken S, Armstrong E G, Gawinowicz Kolks M A G, Cole L A, Agosto G M, Krichevsky A, Vaitukaitis J L and Canfield R E 1988 Endocrinology 123:572–583

Birken S, Canfield R E, Lauer R, Agosto G and Gabel M 1980 Endocrinology 106:1659–1664

Cole L A, Nam J H, Chambers J T, Schwartz P E 1990 Gynecol Oncol 36:391–394

Cole L A, Wang Y, Elliot M, Latef M, Chambers J T, Chambers S K, Schwartz P E 1988a. Cancer Res 48:1356–1360

Cole L A, Schwartz P E, Wang Y X 1988b. Gynecol Oncol 31:82–90

De Lean A, Munson P J and Rodbard D.Am. J. Physiol. 235:E97–E 102. (IBM version of program as distributed by Dr. Peter Munson, Lab. Of theoretical and Physical Biology, NICHD, Bethesda, Md. 20892, 1992).

Ehrlich P, Moyle W R, Moustafa Z A, Canfield RE 1982 Immunol 128:2709–2713

Hartree A S 1975 Methods in Enzymology Vol. XXXVII (O'Malley B W and Hardman J G) Academic Press, NY pp. 381–389

Hoermann, R., Spoett, G. Berger. P. and Mann, K. (1995) Immunoreactive humna chorionic gonadotropin beta core fragment in human pituitary. Exp. Clin. Endocrinol. 103:324–331.

Heyningen V V, Brock D J H, Heyningen S V 1983 J Immunol Meth 62:147–153

Hunter W M and Greenwood F C 1962 Nature 194:495–496

Gomez K A, Retegui L A 1994 Molecular Immunology 31:323–329

Iles R K, Lee C L, Howes I, Davis S, Edwards R, Chard T 1992 J Endocrinol 133:459–166

Kato Y, Braunstein G D 1988 J Clin Endocrinol Metab 66:1197–1201

Kohler G, Milstein C 1975 Nature 256:495–497

Krichevsky A, Birken S, O'Connor J F, Bikel K, Schlatterer J P and Canfield R E 1994 Endocrine 2:511–520

Krichevsky A, Birken S, O'Connor J, Bikel K, Schlatterer J, Yi C, Agosto G and Canfield R 1991 Endocrinology 128:1255–1264

Krichevsky A, Armstrong E G, Schlatterer J, Birken S, O'Connor J, Bikel K, Silverberg S, Lustbader J W and Canfield R E 1988 Endocrinology 123:584–593

Laemmli U K 1953 Nature 227:680–685

Martin-Du-Pan RC, Horak M, Bischof P 1994 Human Reproduction 9:1987–1990

Munson P J and Rodbard D. 1980 Anal. Biochem. 107:220–239 (IBM PC version of program distributed by Dr. Peter Munson, Lab. of Theoretical and Physical Biology, NICHD, Bethesda Md. 20892)

Neven P, Iles R K, Howes I, Sharma K, Shepard J H, Edwards R, Collins W P, Chard T 1993 Clin Chem 39:1857–1860

O'Connor J F, Schlatterer J P, Birken S, Krichevsky A, Armstrong E G, McMahon D and Canfield R E 1988 Cancer Res 48:1361–1366

O'Connor J, Birken S, Lustbader J W, Krichevsky A, Chen Y and Canfield R E 1994 Endocrine Reviews 15:650–683

Odell W D, Griffin J 1987 Clin Chem 33:1603–1607 Petterson K, Ding Y-Q and Huhtaneimi 1992 J Clin Endocrinol Metab 74:164–171.

Petterson K, Ding Y-Q and Huhtaniemi I 1991 Clin Chem 37:1745–1748.

Stanton P G, Pozvek G, Burgon P G, Robertson D M, Hearn M T 1993 J. Endocrinol. 138:529–543.

Wehmann R E and Nisula B C 1981 J Clin Invest 68:184–194

Wehmann R E, Blithe D L, Flack M R and Nisula B C 1989 J Clin Endocrinol Metab 69:510–517.

What is claimed is:

1. The antibody B505 which is produced by the hybridoma designated ATCC No. HB 12000.

2. A hybridoma cell line producing the antibody of claim 1 (ATCC Accession No. HB-12000).

* * * * *